United States Patent [19]
Sendax

[11] Patent Number: 5,749,732
[45] Date of Patent: May 12, 1998

[54] DENTAL IMPLANTATION

[76] Inventor: Victor Sendax, 70 E. 77th St., New York, N.Y. 10021

[21] Appl. No.: 538,680

[22] Filed: Oct. 3, 1995

[51] Int. Cl.$^6$ ........................................ A61C 8/00
[52] U.S. Cl. ................................ 433/174; 433/225
[58] Field of Search ........................ 433/173, 174, 433/221, 225, 220; 606/73

[56] References Cited

U.S. PATENT DOCUMENTS

| | | |
|---|---|---|
| 2,836,890 | 6/1958 | Silvis ................................... 433/174 |
| 3,466,748 | 9/1969 | Christensen .......................... 606/73 |
| 3,499,222 | 3/1970 | Linkow et al. ....................... 433/174 |
| 3,579,830 | 5/1971 | Morel ................................... 433/174 |
| 3,905,109 | 9/1975 | Cohen et al. ......................... 433/174 |
| 4,016,651 | 4/1977 | Kawahara et al. .................... 433/174 |
| 4,182,034 | 1/1980 | McCauley ............................ 433/174 |
| 4,746,294 | 5/1988 | Colombo et al. .................... 433/174 |
| 4,759,714 | 7/1988 | Szeguary ............................. 433/221 |
| 4,780,081 | 10/1988 | Enomoto et al. ..................... 433/174 |
| 4,917,606 | 4/1990 | Miller .................................. 433/225 |
| 5,360,448 | 11/1994 | Thramann ............................ 606/73 |
| 5,527,183 | 6/1996 | O'Brien ............................... 433/174 |
| 5,549,677 | 8/1996 | Dürr et al. ........................... 433/174 |
| 5,575,651 | 11/1996 | Weissman ............................ 433/173 |

OTHER PUBLICATIONS

Journal of American Dental Association, vol. 121, Andreja Baumhammers, DDS, MS—Technique for screw-type implants (Sep. 1996).

Dentistry Today, vol. 14, No. 1, Victor L. Sendax, DDs—Mini Implant Strategy Offers A Broad Range of Uses (Jan. 1995).

*Primary Examiner*—Ralph Lewis
*Attorney, Agent, or Firm*—Sprung Kramer Schaefer & Briscoe

[57] ABSTRACT

A method of placing a denture on a gum in the mouth of a patient so as to be fixed for a prolonged period of time without ready removal by the patient, which comprises a) anesthetizing the area of the patient's gum to be worked upon, b) without flap surgery drilling directly through the gum and into the bone there below a cylindrical bore about 4 to 8 mm in length and of a first diameter, c) withdrawing the drilling implement and inserting into the hole in the gum formed by said drilling an implant of special construction of a diameter larger than said first diameter, the end of the shaft entering said cylindrical bore, d) threading said implant into and beyond said bore to a distance so that approximately only the abutment projects beyond the patient's gum, such abutment constituting a first anchor, e) preparing at least one additional anchor on an element substantially immovably projecting from said gum at a location spaced from said first anchor, and f) forming a denture anchored to said anchors.

The implant is formed of a strong inert metal and comprises a) a threaded shaft having a tapered end and ranging in diameter from about 1 to 2 mm and ranging in length from about 12 to 16 mm, the shaft being integral with a non-circular abutment ranging in length from about 2 to 6 mm.

11 Claims, 2 Drawing Sheets

DENTAL IMPLANTATION

The present invention relates to the provision of a denture which can be worn for long periods of time without removal.

Conventional dentures comprise plastic masses held in the patient's mouth by adhesives and/or metal arms which anchor them to adjacent teeth in the patient's mouth. Such dentures are readily removable and intended to be removed for cleaning, generally daily. Oftentimes they become loose and slip, sometimes even fall out, unintentionally.

Recently there have been developed "fixed" dentures which are not designed to be removed by the patient. They are removable only by the dentist.

While they perform generally satisfactorily, they utilize relatively large "screws" or implants which are threaded into the patient's jaw bone. To use them, the patient's gum is incised and flapped open surgically to expose the bone, large bores are drilled, the implants threaded in with or without projecting heads, and the gums surgically closed about the implant. Generally several such implants are provided along the jaw bone. The projecting heads serve as anchors for "permanent" placement of a denture.

Because of the gum surgery the impression for molding of the denture must await the gums healing and returning to normal dimensions. This could take months. In that time the patient has suffered the pain of the surgery and his/her appearance was usually less than optimal.

Unrelated to artificial dentures, smaller posts have been used by dentists to reinforce teeth on which root canal operations have been performed.

It is an object of the present invention to provide dentures which can satisfactorily remain in place for years without removal.

It is a further object of the invention to provide dentures which can be removed only by the dentist.

These and other objects and advantages are realized in accordance with the present invention pursuant to which there is provided a novel process for placing such a denture in a patient's mouth, immediately irremovable for long periods of time from months or, if desired, up to years.

To that end there is provided a novel mini-implant differing from the large implants normally used in "permanent dentures" and differing also from the smaller posts used in root canal work.

The new mini-implants, like other dental implants, are preferably formed of a strong inert biocompatible metal such as titanium. Such a mini-implant comprises (a) a threaded shaft integral with (b) a non-circular abutment, the implant ranging in overall length from about 15 to 20 mm.

The threaded shaft having a tapered end and ranging in diameter from about 1 to 2 mm and ranging in length from about 12 to 16 mm, the non-circular abutment ranging in length from about 2 to 6 mm.

Advantageously, the shaft along a portion of its surface is not threaded.

More particularly, the shaft along a portion of its surface at a location beginning between about 5 to 8 mm from the shaft end is provided with a flattened area, free of thread, the area in cross-section defining a minor chord of a circle. Advantageously, the chord is at a location from about 10 to 20% of the shaft diameter, and the height of the flattened area in longitudinal direction of the shaft is from about 2 to 5 mm.

In a preferred embodiment, the metal comprises titanium, the implant in overall length is from about 17 to 19 mm, the shaft in diameter is about 1.8 mm and ranges in length from about 3 to 5 mm, the shaft surface for about 3 to 5 mm of its length beginning about 5 to 8 mm from the shaft end is flattened to form in cross section a chord at a location from about 10 to 20% of the shaft diameter.

Most preferably, the mini-implant in total length is about 19 mm, the abutment 5 mm and the shaft 14 mm. The shaft is 1.8 mm in outer diameter and there are about 20 screw threads per cm.

In practicing the process, the dentist first X-rays the patient's gums as precaution against later surprises. The method thereafter comprises the steps of a) anesthetizing the area of the patient's gum to be worked upon, b) without dental flap surgery drilling directly through the gum and into the bone therebelow a cylindrical bore about 4 to 8 mm in length and of a first diameter, c) withdrawing the drilling implement and inserting into the hole in the gum formed by said drilling an implant as described above of a diameter larger than said first diameter, the end of the shaft entering said cylindrical bore.

d) threading said implant into and beyond said bore, self tapping, to a distance so that approximately only the abutment projects beyond the patient's gum, such abutment constituting a first anchor, e) preparing at least one additional anchor on an element substantially immovably projecting from said gum at a location spaced from said first anchor, f) and forming a denture anchored to said anchors.

Advantageously, in step (f) a polymerizable tooth-carrying plastic mass is placed on the anchors, is permitted to auto-polymerize partially on said anchors to form a denture, the denture is withdrawn from the anchors, the polymerized material allowed to set fully, the holes in said denture corresponding to said anchors are enlarged mechanically, polymerizable material is added to said holes, the denture is adjusted for fit, and the polymerizable material is permitted to polymerize and join with the material bonding said holes and to tightly envelop said anchors so that the denture cannot readily be removed from said anchors.

The additional anchor(s) can be stubs of teeth or further standard implant abutments or mini-implants positioned in the same manner. In such latter event, desirably the mini-implants correspond in number and placement approximately to the missing teeth of the patient. If teeth constitute such further anchors they may be re-shaped better to serve as anchors.

As the patient's bone adjusts to the mini-implants in time, the flattened or other non-threaded portion of the shaft reduces any (small) likelihood of unintentional rotation (unthreading) of the implant from the bone it resides in.

The indicated dimensions of the mini-implants makes them especially suited for the instant purpose, not projecting into the bone so far as to create problems but yet forming a firm anchors. The abutment (head) of the implant is short enough to pose no problem with the denture, long enough for proper anchoring.

While a square cross-section is preferred, it could be triangular, hexagonal or of any other shape which permits threaded advance of the shaft by fingers or tool.

Because of their small diameter compared with conventional implants, the novel implants can be placed without gum surgery. A small diameter drill is used to prepare a short cylindrical starting bore, going right through the gum into the jaw bone. Because of its minute diameter there is almost no gum bleeding. As a matter of fact, the minute blood droplet on the gum serves as a marker to assist the dentist in the next step of placing the mini-implant through the gum hole into the hidden-from-view jaw bone.

If desired, several drills of successively increasing diameters, but all still smaller than the mini-implant diameter, may be used. Other tools can be used to thread the mini-implant into the jaw bone.

The implants are advantageously positioned along the apex-line for the jaw bone. While desirably parallel, they might not be absolutely so but this does not pose a problem in the multiple placements and removals of the denture during fitting. Boring out the anchor holes in the denture bottom accommodates each fitting, the final hardening locking the abutment heads in place.

If desired, the dentist can even shape the placed abutment heads if he/she deems it advisable for parallelism.

Returning to implant dimensions, the diameter hereinabove preferred is of the smallest size which permits easy slipping between tooth roots, other implants, avoiding vulnerable structures such as lower jaw nerve, upper jaw sinus and nasal cavities, and cortical bone plates. At the same time the 1.8 mm size is large enough to engage a significant surface area of the useful available bone.

The ultra-small width makes it uniquely possible to be inserted directly through the soft tissue into the underlying bone, without any flap surgery, incisions or sutures, making for a much more patient-friendly procedure than is typical of conventional implant systems.

Further the ultra-slim width permits a minimal encroachment on usually sparse amounts of good quality, tough epithelialized gum tissue, making it all the more likely that the mini-implant will be more comfortable, not only at time of placement but during the after-care period and beyond.

The invention will be further described with reference to the accompanying drawings, wherein.

Figure 1:
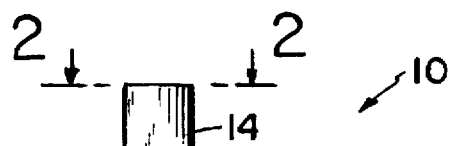
FIG. 1 is a side view of a mini-implant in accordance with the invention, magnified and not to scale.
Figure 3:
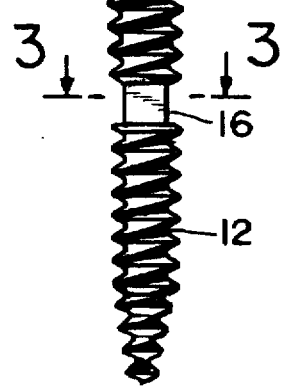
FIG. 3 is a section taken along line 3—3.
Figure 3:
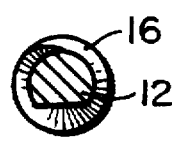
Figure 4:
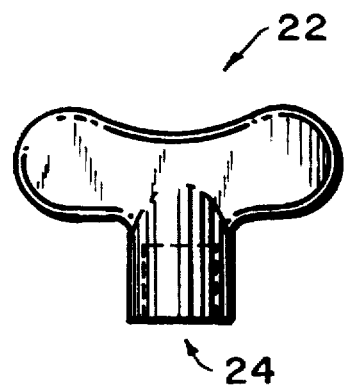
FIG. 4 is a side elevation of a tool for advancing the implant of FIG. 1 into the position of FIG. 5.

Referring now more particularly to the drawing, in FIG. 1 there is shown a mini-implant 10 comprising a threaded cylindrical shaft 12 extending from a tapered end to an abutment 14. The shaft 12 along its length is provided with a short length 16 of non-round configuration, in FIG. 3 shown to be a flattened portion, but which does not interfere with threaded advancement of the shaft, soon to be described.

Figure 2:
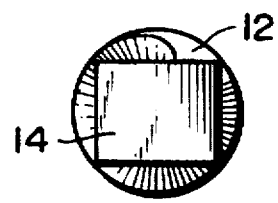
FIG. 2 is a top view of the mini-implant of FIG. 1.

The abutment 14 is of non-round cross-section, desirably square as shown in FIG. 2.

Figure 5:
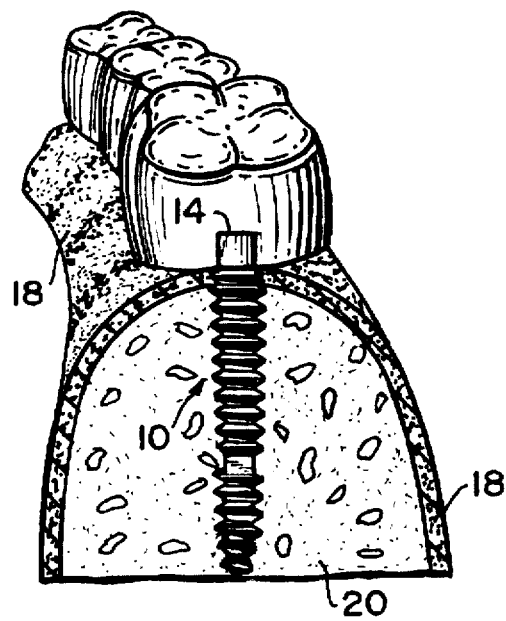
FIG. 5 is a longitudinal transverse sectional view through a patient's gum and jaw bone showing the placement of the abutment of FIG. 1.
Figure 6:
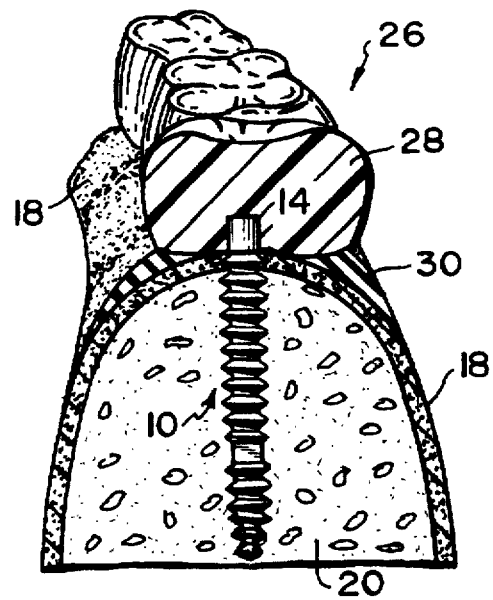
FIG. 6 is a view similar to FIG. 3 showing the denture.

As described hereinbelow, the shaft 12 is inserted through a pre-formed hole in the gum 18 into the top of a pre-formed cylindrical bore in the jaw bone 20. For this purpose there is used a winged tool 22 (FIG. 5) provided with a square recess 24 conforming to abutment 14. Manual rotation of the tool 22 by its wings threadedly advances the implant to the position shown in FIG. 5. The projecting abutment 14 constitutes an anchor which, together with at least one further anchor, serves to hold in place a denture 26, comprising artificial teeth 28 and a gum-hugging apron 30 (FIG. 6).

Figure 7:
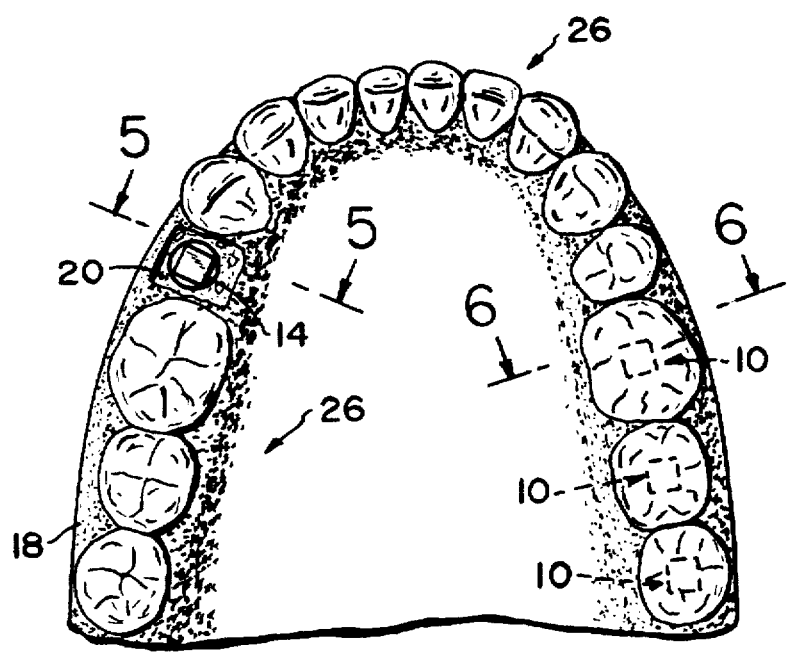
FIG. 7 is a perspective view of a patient's jaw bone showing the fixed denture and, in phantom, a multiplicity of implants according to FIG. 1.

In FIG. 7 there is shown the jaw bone 20 carrying the denture 26 anchored in place by several mini-implants 12.

The following non-limiting examples illustrate practice of the present invention:

EXAMPLE 1

On the day of implant insertion the patient was anesthetized with a local injection for gum tissue only (bone is not usually sensitive enough to require anesthesia for such small implants avoiding a block anesthetic which numbs up the whole jaw and which patients dislike). A pilot drill was used to pierce the gum tissue and enter the bone for a few millimeters to test the bone quality (soft or hard) and to evaluate the direction of drill placement relative to available bone and any surrounding vulnerable structures such as adjacent teeth or implants, marrow spaces or old defect spaces, nerve branches in lower jaw, sinus or nasal floors in upper jaw, outer or inner hard layers of bone (cortices to avoid unwanted perforations, as well as to insure parallel or as near to parallel positioning of the mini-implants themselves. Once determined, the regular drill size (smallest available Lindemann type bone drill) was used to drill approximately 7 mm into the bone site and the post implant was test inserted into the drilled hole (through gum tissue and bone) using a winged nut with a square recess until the full 14 mm shaft of the implant was screwed into the bone. Seven more such implants were screwed into the lower jaw at spaced locations to provide eight mini-implants in total, supplementing a pre-existing single tooth root on the lower right side and two pre-existing original blade type implants that had survived from prior treatments. All these supports were then tested for stability and comfort. The patient's removable lower jaw denture which was unsatisfactory to the patient because of constant movement instability when talking, singing, and chewing, was then hollowed out with a large denture reamer-drill to provide internal room (i.e. clearance) for the implant heads when placed in the mouth over these heads. When proper clearance was established the inside of the removable denture was then relined with fast-cure pink denture acrylic, replaced in the mouth, the biting relationship with the upper teeth manipulated by moving the denture around slightly until good bite conformation was achieved, and the denture taken on and off several times with the patient carefully instructed and guided to close into a normal closed bite position, and then the denture finally removed before the acrylic polymerized (set) and allowed to cure on the laboratory bench. Once set, the multiple implant head (and the single tapered natural tooth preparation) sites in the denture undersurface were reamed out to provide ease of insertion and removal over all the support elements, eliminating the non-parallel binding that would have otherwise prevented such seating. A small amount of additional cold-cure acrylic was applied to these individual sites (9 total) with the standard brush-on technique using powder (polymer resin) and liquid (monomer) and the denture reinserted over the post-implant heads directly in the mouth of the patient. The patient was instructed to close into normal hinged biting position with lower jaw in normal retracted (retruded) position to check the bite relationship, slight corrections of position were made as required and then the patient sat teeth closed, for about 10 minutes for the acrylic to harden and lock the denture to the underlying post-implants (and single tooth pre-prepared post-abutment). When set a final bite adjustment was made in the classic method using articulating carbon paper to transfer any premature uneven biting contacts to the upper and lower tooth surfaces and the bite then adjusted by selective reshaping of the tooth surfaces using diamond drills according to standard methodology. Careful adjustment of the now fixed denture contours were also made at the same time for good hygiene and to avoid any impingements on the surrounding gum tissue. The patient was then discharged.

EXAMPLE 2

Local anesthetic injections for gum tissue were performed. The fractured tooth roots were smoothed, fragments removed and the remaining support teeth were prepared for abutments. Mini-implants were then inserted wherever there appeared to be available bone to supplement any usable tooth supports, using the same insertion protocol as in Example 1. The patient's original fractured-out bridge was cleaned out and modified to receive the heads of the mini-Implants and any remaining tooth abutments. The internal surfaces of crown supports of an existing bridge were then relined with self-curing methyl methacrylate acrylic resin using the same protocol described in Example 1. The bridge was then finally inserted using additional small amounts of self-curing acrylic resin. The bite was adjusted to provide a stable biting pattern to avoid uneven prematurities that probably contributed originally to the patient's problem and fracturing out of the teeth from the mouth. The patient then returned the following day for minor adjustments.

EXAMPLE 3

Local anesthetic injections were administered. Mini-implants were placed around the lower jaw arch as in Example 1.

The patient's own existing lower denture was then refined and adjusted for good adaptation to the patient's bone and gum tissues and then was internally reamed out to provide clearance for the mini-implant heads. Rebasing, and final bonding of the bridge to the implant heads using cold self-curing acrylic resin as in Example 1 was effected. The bite was adjusted accordingly and the patient returned for two post-insertion adjustment visits and bite refinements which were routine procedures. The patient has experienced no pain or discomfort since the initial insertion visit and has returned for basic cleaning-oral hygiene maintenance visits without incident.

X-rays have confirmed for all three Examples the durability of the devices themselves, the superstructures (bridge teeth) and the underlying bone gum stability.

It will be understood that the specification and examples are illustrative but not limitative of the present invention and that other embodiments within the spirit and scope of the invention will suggest themselves to those skilled in the art.

What I claim is:

1. A dental mini-implant comprising a shaft having two opposite ends, one of which is tapered and the other of which is connected to a non-circular abutment, wherein, (A) the shaft ranges in diameter from about 1 mm to about 2 mm and in length from about 12 mm to about 16 mm;

(B) a portion along a surface of the shaft at a location beginning between 5 mm to 8 mm from the tapered end is provided with a flattened area, free of thread, the flattened area in cross-section defining a chord of a circle;

(C) the shaft being threaded essentially over its entire length except for said portion in (B);

(D) the non-circular abutment ranges in length from about 2 mm to about 6 mm; and (E) the dental mini-implant ranges in overall length from about 15 mm to about 20 mm.

2. An implant according to claim 1, wherein the length of the flattened area in longitudinal direction of the shaft is from about 2 to 5 mm.

3. An implant according to claim 1, wherein the metal comprises titanium, the implant in overall length is from about 17 to 19 mm, the shaft in diameter is about 1.8 mm and ranges in length from about 13 to 15 mm, the abutment is approximately square in cross-section and ranges in length from about 3 to 5 mm, the shaft surface for about 3 to 5 mm of its length beginning about 5 to 8 mm from the shaft end is flattened to form in cross section defining a chord of a circle.

4. A method of anchoring a denture in the jaw bone in the mouth of a patient in need of such method using an implant so as to be fixed for a prolonged period of time without ready removal by the patient, which comprises a) anesthetizing the area of the patient's gum to be worked upon, b) without surgery drilling with a drilling implement directly through the gum and into the bone there below a cylindrical bore about 4 to 8 mm in length and of a first diameter, c) withdrawing the drilling implement and inserting into the hole in the gum formed by said drilling an implant of a diameter larger than said first diameter, the end of the shaft entering said cylindrical bore, d) threading said implant into and beyond said bore to a distance so that approximately only the abutment projects beyond the patient's gum, such abutment constituting a first anchor, e) preparing at least one additional anchor on an element substantially immovably projecting from said gum at a location spaced from said first anchor, and f) forming a denture anchored to said anchors, wherein said implant comprises a shaft having two opposite ends, one of which is tapered and the other of which is connected to a non-circular abutment, and wherein;

(A) the shaft ranges in diameter from about 1 mm to about 2 mm and in length from about 12 mm to about 16 mm;

(B) a portion along a surface of the shaft at a location beginning between 5 mm to 8 mm from the tapered end is provided with a flattened area, free of thread, the flattened area in cross-section defining a chord of a circle;

(C) the shaft being threaded essentially over its entire length except for said portion in (B);

(D) the non-circular abutment ranges in length from about 2 mm to about 6 mm; and (E) the dental mini-implant ranges in overall length from about 15 mm to about 20 mm.

5. The method according to claim 4, wherein said at least one additional anchor comprises at least one additional implant positioned by steps (b), (c) and (d).

6. The method according to claim 5, wherein the implants correspond in number and placement approximately to the missing teeth of the patient.

7. The method according to claim 6, wherein the metal of the implant comprises titanium, the implant in overall length is from about 17 to 19 mm, the shaft in diameter is about 1.8 mm and ranges in length from about 12 to 16 mm, the shaft surface for about 3 to 5 mm of its length beginning about 5 to 8 mm from the shaft end is flattened to form in cross section defining a chord of a circle.

8. A method of anchoring a denture in the jaw bone in the mouth of a patient in need of such method using an implant so as to be fixed for a prolonged period of time without ready removal by the patient, which comprises a) anesthetizing the area of the patient's gum to be worked upon,
 b) without surgery drilling with a drilling implement directly through the gum and into the bone there below a cylindrical bore about 4 to 8 mm in length and of a first diameter,
 c) withdrawing the drilling implement and inserting into the hole in the gum formed by said drilling an implant of a diameter larger than said first diameter, the end of the shaft entering said cylindrical bore,
 d) threading said implant into and beyond said bore to a distance so that approximately only the abutment projects beyond the patient's gum, such abutment constituting a first anchor,
 e) preparing at least one additional anchor on an element substantially immovably projecting from said gum at a location spaced from said first anchor, and
 f) forming a denture anchored to said anchors;
wherein in step (f)
 a polymerizable tooth-carrying plastic mass is placed on the anchors, is permitted to polymerize partially on said anchors to form a denture, the denture is withdrawn from the anchors, the holes in said denture corresponding to said anchors are enlarged mechanically, polymerizable material is added to said holes, the denture is adjusted for fit, and the polymerizable material is permitted to polymerize and join with the material bounding said holes and to tightly envelop said anchors so that the denture cannot readily be removed from said anchors;

wherein said implant comprises a shaft having two opposite ends, one of which is tapered and the other of which is connected to a non-circular abutment, and wherein;

(A) the shaft ranges in diameter from about 1 mm to about 2 mm and in length from about 12 mm to about 16 mm;
 (B) a portion along a surface of the shaft at a location beginning between 5 mm to 8 mm from the tapered end is provided with a flattened area, free of thread, the flattened area in cross-section defining a chord of a circle;
 (C) the shaft being threaded essentially over its entire length except for said portion in (B);
 (D) the noncircular abutment ranges in length from about 2 mm to about 6 mm; and
 (E) the dental mini-implant ranges in overall length from about 15 mm to about 20 mm.

9. The method according to claim 8, wherein said at least one additional anchor comprises at least one additional implant positioned by steps (b), (c) and (d).

10. The method according to claim 9, wherein the implants correspond in number and placement approximately to the missing teeth of the patient.

11. The method according to claim 10, wherein the metal of the implant comprises titanium, the implant in overall length is from about 17 to 19 mm, the shaft in diameter is about 1.8 mm and ranges in length from about 12 to 16 mm, the shaft surface for about 3 to 5 mm of its length beginning about 5 to 8 mm from the shaft end is flattened to form in cross section defining a chord of a circle.

\* \* \* \* \*